United States Patent [19]

Herold et al.

[11] Patent Number: 4,839,566
[45] Date of Patent: Jun. 13, 1989

[54] CIRCUIT FOR SUPPLYING POWER TO A DENTAL PHOTOPOLYMERIZING APPARATUS

[75] Inventors: Wolf-Dietrich Herold, Seefeld; Karl L. Grafwallner, Munich; Michael Keller, Graefelfing, all of Fed. Rep. of Germany

[73] Assignee: ESPE Stiftung and Co. Produktions-und Vertriebs KG, Seefeld, Fed. Rep. of Germany

[21] Appl. No.: 16,601

[22] Filed: Feb. 19, 1987

[30] Foreign Application Priority Data

Feb. 19, 1986 [DE] Fed. Rep. of Germany ....... 3605278

[51] Int. Cl.⁴ .................................................. H05B 37/02
[52] U.S. Cl. ........................................ 31/308; 315/307; 315/209 R; 315/DIG. 7; 315/150; 315/241 P; 315/241 S; 315/291; 128/395; 250/493.1; 250/504 R
[58] Field of Search .................. 315/307, 308, 209 R, 315/208, 224, 149, 150, 151, 156, 158, 194, DIG. 7; 250/504 R, 493.1; 382/55, 50; 128/303.1, 362, 395, 397, 398

[56] References Cited

U.S. PATENT DOCUMENTS

| | | | |
|---|---|---|---|
| 3,573,543 | 4/1971 | Grindstaff | 315/194 |
| 4,149,086 | 4/1979 | Nath | 250/504 |
| 4,275,335 | 6/1981 | Ishida | 315/209 R |
| 4,289,972 | 9/1981 | Wern | 315/362 |
| 4,300,075 | 11/1981 | Foose et al. | 315/307 |
| 4,358,717 | 11/1982 | Elliott | 315/208 |
| 4,359,669 | 11/1982 | Anderson | 315/208 |
| 4,375,045 | 2/1983 | Yim | 315/209 R |
| 4,379,254 | 4/1983 | Hurban | 315/291 |
| 4,412,156 | 10/1983 | Ota | 315/308 |
| 4,414,493 | 11/1983 | Henrich | 315/308 |
| 4,422,016 | 12/1983 | Kurple | 315/308 |
| 4,503,364 | 3/1985 | Engel | 315/308 |

FOREIGN PATENT DOCUMENTS 3411994 10/1985 Fed. Rep. of Germany.

*Primary Examiner*—David K. Moore
*Assistant Examiner*—Michael Razaui
*Attorney, Agent, or Firm*—Foley & Lardner, Schwartz, Jeffery, Schwaab, Mack, Blumenthal & Evans

[57] ABSTRACT

An electric lamp for the photopolymerization of dental materials is supplied with constant electric power so that constant light output is obtained. The control circuit used to this end operates with a triac (3) connected between an a.c. voltage supply (2) and the lamp (1), said triac being controlled by signal values stored in a read-only memory of a microprocessor (4). Said stored values are respectively allocated to pairs of instantaneous values of lamp current and lamp voltage, the instantaneous values being detected in each cycle of the a.c. supply voltage and being utilized to address the read-only memory.

7 Claims, 1 Drawing Sheet

CIRCUIT FOR SUPPLYING POWER TO A DENTAL PHOTOPOLYMERIZING APPARATUS

The invention concerns a circuit for supplying power to a dental photopolymerizing apparatus.

Radiation apparatus of this type are known and comprise lamps, in particular low-voltage halogen lamps, which emit UV-light or near-UV blue light which is directed by an optical wave guide or the like to the site of treatment in a patient's mouth for curing a filling. For achieving reliable, uniform photopolymerization it is essential that irrespective of variations in the supply voltage of the lamp a quantity of light, which is always constant as to quality and quantity, is produced during each polymerization cycle which lasts, for instance, 20 seconds.

This objective cannot be achieved by using a constant voltage source. Due to maufacturing tolerances, especially in respect of the geometry of the tungsten filament, lamps having the same rated wattage may vary relatively widely in their electric power input as measured at constant voltage. According to maufacturer's specifications the variations may be up to 12%. In view of the fact that even slight changes in electric power input will cause relatively large variations of the emitted UV-radiation and near-UV-radiation of the lamp, replacement of a lamp may already cause an undesirably large variation of the luminous flux. As explained in U.S. Pat. No. 4,149,086, variations of the lamp voltage amounting to ±5% will cause fluctuations of as much as ±20% in the UVemission.

Furthermore, in the course of time, burn-off will occur at the tungsten filament of a halogen lamp, whereby the electric resistance of the filament progressively increases. When the lamp is supplied with power from a constant voltage source, the current and thus the electric output and consequently also the radiation output will decrease.

An attempt to counteract voltage fluctuations and the resulting light variations by a constant current supply of the lamp will not meet with success either. Again, upon exchange of a lamp there may be considerable differences as to the light output. Furthermore, in the case of constant current supply, when the electric resistance of the filament increases due to burn-off, the voltage will change accordingly so that now the electric power input will increase and the luminous flux will increase super-proportionally, whereby the life of the lamp is drastically shortened.

German Offenlegungsschrift No. 3,411,994 proposes to obtain a constant light output by providing a second lamp as a reference light source connected in parallel to the irradiation lamp proper, said second lamp illuminating a photodetector the output signal of which is used to control the irradiation lamp voltage. This control has the fundamental drawback that the two lamps may have different characteristics such as dependency of the light output on the lamp voltage, aging, etc., so that even with uniform light output of the reference lamp the light output of the irradiation lamp may vary. Furthermore, the known circuit is unable to recognize the different electric input and thus the different light output of a new lamp or to compensate for a decrease in the lamp current and thus in the luminous flux of the irradiation lamp due to filament burnoff. The control will be further corrupted by progressively varying characteristics of the photodetector due to aging. Finally, to inhibit influences resulting from the temperature sensitivity of reference lamp and detector it is necessary to accomodate these components together with a temperature compensating resistor in a thermally sealed-off environment, thus making the irradiation apparatus complex.

It is an object of the invention to provide a circuit for supplying power to the lamp of a dental photopolymerization apparatus which makes it possible to obtain qualititatively and quantitatively uniform light output throughout the life of the lamp with the lamp life being maximum.

This object is met in accordance with the invention in that control means is provided which maintains the electric power input to the lamp constant.

DESCRIPTION OF THE PREFERRED EMBODIMENT

The invention is based on the finding that the light output of the lamp remains practically constant irrespective of fluctuations of the supply voltage and variations of the filament resistance such as caused by burn-off, provided the electric power input is maintained constant. This can be explained with reference to the lamp wattage distribution for tungstenhalogen lamps by means of the following equation:

$$P_{el} = \Lambda \cdot T + \sigma \cdot T^4 \cdot A$$

wherein

| | |
|---|---|
| $P_{el}$ | electric power input |
| $\Lambda \cdot T$ | power dissipated by thermal conduction |
| $\sigma \cdot T^4 \cdot A$ | power dissipated by radiation (light output) |
| $\Lambda$ | thermal conductivity |
| T | absolute temperature |
| $\sigma$ | Stefan-Boltzmann constant |
| A | radiating filament surface |

Considering the case of constant voltage with reference to the above equation, it will be apparent that with burn-off of the tungsten filament, the current density and thus the temperature T of the filament material will not change due to the constant voltage. The light output $\sigma \cdot T^4 \cdot A$ is thus directly dependent on the filament surface A. When the electric power input $P_{el}$ decreases, the light output will decrease proportionally, as illustrated in FIG. 1 with reference to the characteristic U=const.

It will also be apparent that with new lamps of the same rated wattage different light outputs will result in direct dependency on the filament diameter or filament resistance, respectively. As mentioned above, variations of power input amount to up to 12% with new lamps as specified by manufacturers; additionally, there results an electric power decrease and in conjunction therewith a decrease in the light output of about 20% during the lamp life.

Considering the above equation for the case of constant current, on the other hand, the current density and thus the temperature T will increase with burn-off of the filament. While the radiation filament surface A will become smaller, this loss will be overcompensated since the temperature T stands to the power of four. Thereby the light output $\sigma.T^4.A$ will increase super-proportionally and the life of the filament will rapidly decrease (cf. curve I=const in FIG. 1).

Figure 1:
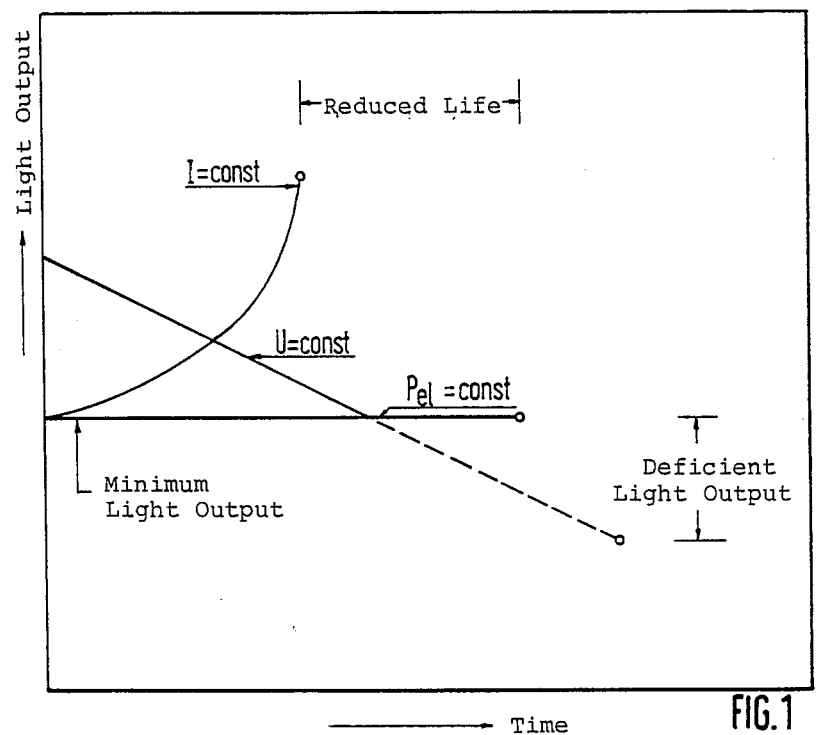
FIG. 1, illustrates the decrease of electric power input pel and the decrease of the light output.

At constant current operation, the curve I=const of FIG. 1 will also hold for new lamps, which will thus widely vary in light output.

Considering the above equation with a view to constant electric power input $P_{el}$ it will be apparent that a reduction in the filament surface A caused by burn-off only results in an extremely slight variation of the temperature T (viz. to the extent of the fourth root) so that the power $A.T$ dissipated by heat will likewise change only very slightly, and the light output $\sigma.T^4.A$ can be regarded as nearly constant. Thus, an approximately constant light output will be obtained throughout the life of the lamp is illustrated by the characteristic $P_{el}$=const in FIG. 1.

It will be further apparent from FIG. 1 that with a required minimum light output $\sigma.T^4.A$ a lamp operated at a constant electric power input $P_{el}$ will have maximum life, which is an important aspect in view of ecomonic operation.

Other objects of the invention reside in obtaining a constant electric power with minimum loss, minimum circuit design effort and fast response.

In some prior art circuits for controlling the electric output of a lamp, a d.c. voltage supply for the lamp is used, wherein lamp current and lamp voltage are correlated and control is effected such that the excess power made available by the power source is converted to heat. Apart from an undesirable increase in the temperature of the control device, this signifies a very inferior efficiency. On the other hand, if an a.c. voltage supply is used, it will be possible to realize an almost no-loss control by means of phase control. In this case, because the actual lamp current and voltage are not in the form of sinusoidal signals, they are for further processing regularly converted to d.c. voltage values the level of which corresponds to the effective values of lamp current and voltage. This implies a considerable circuit design effort and a correspondingly slow-acting control operation because of the required capacitances.

The circuit of this invention as specified below does not require rectification and operates directly with instantaneous values, preferably the peak values, of the lamp current and lamp voltage, since these peak values are representative of the effective values of lamp current and lamp voltage, provided that the a.c. supply voltage has a largely sinusoidal characteristic. Consequently, a phase control angle dependent on these instantaneous values is required for obtaining a constant effective value, i.e. constant wattage. This dependence is stored in tabular form in the read-only memory of a microprocessor for different instantaneous values of lamp current and lamp voltage. In each cycle of the a.c. supply voltage the peak value of the lamp current and the peak value of the lamp voltage are detected and a corresponding signal value for the combination of these two values is read out from the memory and is used to provide the phase control angle for the nextfollowing cycle.

The circuit of this invention may be used not only in the dental field but also for controlling polymerization lamps for other technical applications, and it may also be used in conjunction with colorimeters, still and film projectors and copying apparatus, and generally wherever a constant electric output is required.

In a preferred embodiment, means is provided to detect extreme values of lamp current and/or lamp voltage, which may occur when the supply voltage is too high or too low, in case of a short-circuit or during no-load operation (faulty lamp), and to cause the lamp to be turned off.

In another development of the invention, a so-called "soft start" is achieved which is intended to protect the lamp and which causes the lamp voltage to rise slowly when the lamp is turned on; thereby any starting current surge is prevented which would otherwise be caused by the extremely low resistance of the cold filament.

Below, an embodiment of the invention will be described with reference to FIG. 2, which is a block diagram of a circuit for supplying a lamp with constant electric power.

Figure 2:
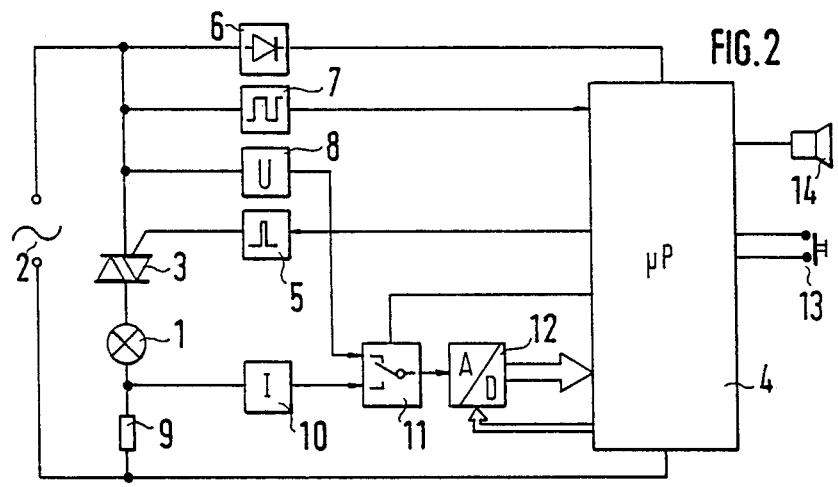
FIG. 2 is a schematic block diagram of a circuit for supplying a lamp with constant electric power.

According to FIG. 2 a lamp 1 is supplied by an a.c. voltage source 2. A triac 3 is used to maintain the electric power supplied to the lamp 1 at a constant value, a control signal being applied to the gate electrode of said triac from a microprocessor 4 through a trigger circuit 5. The microprocessor 4 is supplied through a rectifier 6 from the a.c. voltage source 2 and is synchronized to the frequency thereof by a synchronizing circuit 7. The lamp voltage is detected by a detection circuit i, and the lamp current is derived via a detection circuit 10 as the voltage drop occurring across a shunt 9. The output signals from the two detection circuits 8 and 10 are applied to the two inputs of an electronic changeover-switch 11 the output signal of which is supplied via an analog-to-digital converter 12 to the microprocessor 4. The changeover-switch 11 is driven by the microprocessor 4 in synchronism with the frequency of the a.c. voltage supply 2 so that in each cycle the detected values of lamp current and lamp voltage are applied to the analog-to-digital converter 12 which in its turn is controlled by the microprocessor 4 such that it performs conversion of the respective detected value at the time when the same is at maximum amplitude. The two detected values of lamp current and lamp voltage are supplied to the microprocessor 4 in digital form and used to address a read-only memory disposed in the microprocessor, which memory stores signal values representative of phase control angles of said triac 3 in the form of a two-dimensional table. In response to a given pair of lamp current and lamp voltage values, the microprocessor 4 will thus provide the corresponding phase control angle value as an input signal to the trigger circuit 5.

Upon depression of a starting pushbutton 13 a soft start is initiated, wherein the processor 4 provides for continuous shifting of the trigger pulse for the triac 3 from 180° towards 0°. During the soft start the lamp current is continually monitored so that in case of a short circuit in the lamp the soft start will be interrupted and a signal generator 14 will produce an alarm signal.

When there is no malfunction during the soft start, a state of constant output control will be adopted. After a predetermined irradiation period has elapsed, the microprocessor 4 stops the pulses delivered to the trigger circuit 5 and causes the signal generator 14 to produce an end signal which is distinctly different in frequency from the alarm signal.

Since the lamp current and the lamp voltage are detected during each cycle of the a.c. supply voltage and are used to control the triac, fast control is ensured. Any extreme values of lamp current and lamp voltage such as may be caused by variations in the a.c. voltage source 2, by an improper lamp or by other irregularities are recognized by the microprocessor 4; in that case it will also stop supplying control pulses to the trigger circuit 5 and cause the signal generator 14 to deliver an alarm signal.

We claim:

1. A circuit for supplying power to a low-voltage lamp of a type used in a photopolymerizing apparatus from an a.c. voltage source comprising:

control means for keeping the electric power input to said low-voltage lamp constant, said control means including a memory for storing signal values representative of a plurality of different duty factors predetermined for respective pairs of different values of lamp current and lamp voltage;

first means for continuously detecting the lamp voltage and generating a first output signal indicative thereof;

second means for continuously detecting the lamp current and generating a second output signal indicative thereof;

sampling means synchronized with said a.c. voltage for sampling instantaneous values of said first and second output signals in each cycle of said a.c. voltage "converting the sampled instantaneous values to digital output signals" and supplying the digital output signal to said control means; and a switching element, controlled by a signal value read from said memory by said control means based on the sampled values received from said sampling means and supplied to said switching element, for switching the lamp current on and off in cycles synchronous with said a.c. voltage from said a.c. voltage source with a duty factor dependent on the lamp current and lamp voltage.

2. The circuit of claim 1, wherein said switching element is a triac having its gate electrode controlled by the respective signal value read from said memory.

3. The circuit of claim 1, wherein said sampling means is controlled so as to sample the peak values of the output signals of both said detecting means in each cycle of the a.c. supply voltage.

4. The circuit of claim 1, wherein said circuit comprises an electronic change-over switch synchronized with the a.c. supply voltage having two inputs each connected to one of said detecting means and an output connected to an analog-to-digital converter, said analog-to-digital converter being driven in synchronism with the a.c. supply voltage.

5. The circuit of claim 4, wherein said switching element, said change-over switch, said analog-to-digital converter, and said address control of said memory are controlled by a microprocessor which is synchronized with the a.c. supply voltage.

6. The circuit of claim 1, comprising means for switching off said lamp upon occurrence of one of the following conditions:

(a) the lamp current leaves a predetermined range of current values, (b) the lamp voltage leaves a predetermined range of voltage values.

7. The circuit of claim 1, comprising means for decreasing the rate of lamp voltage rise during turning-on of said lamp.

* * * * *